(12) United States Patent
Soundarrajan et al.

(10) Patent No.: US 7,695,609 B2
(45) Date of Patent: *Apr. 13, 2010

(54) NANOBIOSENSOR AND CARBON NANOTUBE THIN FILM TRANSISTORS

(75) Inventors: Prabhu Soundarrajan, Valencia, CA (US); James Novak, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/134,030

(22) Filed: Jun. 5, 2008

(65) Prior Publication Data

US 2008/0302676 A1 Dec. 11, 2008

Related U.S. Application Data

(63) Continuation of application No. 10/952,669, filed on Sep. 29, 2004, now Pat. No. 7,399,400.

(60) Provisional application No. 60/507,436, filed on Sep. 30, 2003, provisional application No. 60/598,293, filed on Aug. 3, 2004.

(51) Int. Cl.
G01N 27/327 (2006.01)
G01N 27/414 (2006.01)

(52) U.S. Cl. .............. 205/777.5; 205/775; 205/792; 204/403.01; 204/403.06; 204/403.14; 435/4; 435/6; 435/25; 977/920; 977/957

(58) Field of Classification Search .......... 204/406, 204/403.14, 403.01, 403.06, 175; 205/785.5, 205/777.5, 775; 435/4, 6, 287.1; 324/71.1
See application file for complete search history.

(56) References Cited

U.S. PATENT DOCUMENTS

| 4,694,834 | A | 9/1987 | Meyerhoff et al. |
| 6,249,326 | B1 | 6/2001 | Hebiguchi |
| 6,656,712 | B1 | 12/2003 | Balavoine et al. |
| 6,894,359 | B2 | 5/2005 | Bradley et al. |
| 6,905,655 | B2 | 6/2005 | Gabriel et al. |
| 6,918,284 | B2 | 7/2005 | Snow et al. |
| 2002/0086335 | A1 | 7/2002 | Massey et al. |
| 2002/0172963 | A1 | 11/2002 | Kelley et al. |

(Continued)

FOREIGN PATENT DOCUMENTS

DE 10102657 1/2003

(Continued)

OTHER PUBLICATIONS

Star et al. (Electronic Detection of Specific protein binding using nanotube FET devices), Nano Letters, vol. 3, No. 4, Mar. 2003, pp. 459-463.*

(Continued)

*Primary Examiner*—Nam X Nguyen
*Assistant Examiner*—Jennifer Dieterle
(74) *Attorney, Agent, or Firm*—Kelly Kordzik; Matheson Keys; Garsson & Kordzik PLLC

(57) ABSTRACT

The present invention is directed to systems and methods for detecting biological and chemical species in liquid and gaseous phase. The systems and methods utilize carbon nanotubes to enhance sensitivity and selectivity towards the reacting species by decreasing interference and detecting a wide range of concentrations.

11 Claims, 8 Drawing Sheets

U.S. PATENT DOCUMENTS

| | | | |
|---|---|---|---|
| 2003/0207326 | A1 | 11/2003 | Su et al. |
| 2004/0149578 | A1 | 8/2004 | Huang |
| 2004/0200734 | A1* | 10/2004 | Co et al. .................. 205/777.5 |
| 2004/0261500 | A1 | 12/2004 | Ng et al. |
| 2005/0244811 | A1 | 11/2005 | Soundarrajan et al. |

FOREIGN PATENT DOCUMENTS

| | | |
|---|---|---|
| EP | 0585113 | 3/1994 |
| EP | 0634488 | 1/1995 |
| EP | 1211507 A2 | 6/2002 |
| JP | 2002071620 | 3/2002 |
| JP | 2002-195997 | 7/2002 |
| JP | 2003-100639 | 4/2003 |
| WO | WO 01/38873 | 5/2001 |
| WO | WO 01/43870 | 6/2001 |
| WO | WO0248701 | 6/2002 |
| WO | WO03/016901 | 2/2003 |
| WO | WO 03/087798 | 10/2003 |
| WO | WO03/087798 A1 | 10/2003 |

OTHER PUBLICATIONS

Gao et al. (Biosenosrs based on aligned carbon nanotubes coated with inherently conducting polymers), Electroanalysis, vol. 15, No. 13, Aug. 2003, pp. 1089-1094.*

Sotiropoulou, et al., "Carbon nanotube array-based biosensor", *Anal. Bioanal. Chem.*, Jan. 2003, vol. 375, No. 1, pp. 103-105.

Cai, et al., "Carbon nanotube-enhanced electrochemical DNA biosensor for DNA hybridization detection," *Anal. Bional. Chem.*, Jan. 4, 2003, vol. 375, pp. 287-293.

Jianrong, et al., "Nanotechnology and biosensors," *Biotechnology Advances*, Sep. 2004, vol. 22, No. 7, pp. 505-518.

Huang, et al., "Immobilization of antibodies and bacterial binding on nanodiamond and carbon nanotubes for biosensor applications," *Diamond and Related Materials*, Apr. 2004, vol. 13, No. 4-8, pp. 1098-1102.

Atashbar, et al., "SWNT Network for Biomolecule Detection," *Mater. Res. Soc. Symp. Proc.*, 2004, vol. 858, pp. 313-318.

Bradley, et al., "Change Transfer From Adsorbed Proteins," Nano Letters, Jan. 8, 2004, vol. 4, No. 2, pp. 253-256, American Chemical Society.

Chen, et al., "Noncovalent Sidewall Functionalization of Single-Walled Carbon Nanotubes For Protein Immobilization," J. Am. Chem. Soc., 2001, vol. 123, No. 16, pp. 3838-3839, American Chemical Society.

Dai et al., "Sensors and Sensor Arrays Based On Conjugated Polymers and Carbon Nanotubes," Pure Appl. Chem, 2002, vol. 74, No. 9, pp. 1753-1772, International Union of Pure and Applied Chemistry.

"Potentiostat Primer", 5 pages [www.gamry.com/App_Notes/potentiostat_primer.htm], Gamry Instruments, Last Revised on May 19, 2005.

Soundarrajan, et al., "Surface Modification of Aligned Carbon Nanotube Arrays For Electrochemical Sensing Applications," J.Vac. Sci. Technology A., Jul./Aug. 2003, vol. 21, No. 4, pp. 1198-1201, American Vaccum Society.

Star, et al., "Electronic Detection of Specific Protein Binding Using Nanotube FET Devices," Nano Letters, 2003, vol. 3, No. 4, pp. 459-463, American Chemical Society.

Jiang Zhu et al., "Improving the Dispersion and Integration of Single-Walled Carbon Nanotubes in Epoxy Composites through Functionalization," *Nano Letters*, 2003, vol. 3, No. 8, pp. 1107-1113.

Lei Zhang et al., "Sidewall Functionalization of Single-Walled Carbon Nanotubes with Hydroxyl Group-Terminated Moieties," *Chem. Mater.*, 2004, vol. 16, pp. 2055-2061.

E. S. Snow et al., "Random networks of carbon nanotubes as an electronic material," *Applied Physics Letters*, vol. 32, No. 13, Mar. 31, 2003, pp. 2145-2147.

J. P. Novak et al., "Macroelectronic applications of carbon nanotube networks," *Solid State Electronics*, vol. 48, 2004, pp. 1753-1756.

Marcus D. Lay et al., "Simple Route to Large-Scale Ordered Arrays of Liquid-Deposited Carbon Nanotubes," *Nano Letters*, vol. 4, No. 4, 2004, pp. 603-606.

C. A. Furtado et al., "Debundling and Dissolution of Single-Walled Carbon Nanotubes in Amide Solvents," *J. Am. Chem. Soc.*, vol. 126, 2004, pp. 6095-6105.

Rajdip Bandyopadhyaya et al., "Stabilization of Individual Carbon Nanotubes in Aqueous Solutions," *Nano Letters*, vol. 2, No. 1, 2002, pp. 25-28.

S. Saini et al., "Preliminary investigation of a bioelectrochemical sensor for the detection of phenol vapours," *Biosensors and Bioelectronics*, vol. 10, 1995, pp. 945-957.

Silvia A. Miscoria, "Analytical Performance of a Glucose Biosensor Prepared by Immobilization of Glucose Oxidase and Different Metals into a Carbon Paste Electrode," *Electroanalysis*, 14, No. 14, 2002, pp. 981-987.

Gao, M., Dai, L., And Wallace, G. G., "Biosensors Based on Aligned Carbon Nanotubes Coated with Inherently Conducting Polymers," Electroanalysis, 15, No. 13, Aug. 2003, pp. 1089-1094.

Eun Jeong Cho et al., "Multianalyte Pin-Printed Biosensor Arrays Based on Protein-Doped , Xerogels," *Analytical Chemistry*, vol. 74, No. 24, Dec. 15, 2002, pp. 6177-6184.

Christophe A. Marquette et al., "Electrochemiluminescent biosensors array for the concomitant detection of choline, glucose, glutamate, lactate, lysine and urate," *Biosensors and Bioelectronics*, vol. 19, 2003, pp. 433-439.

S. Sapelnikova et al., "Screen-printed multienzyme arrays for use in amperometric batch and flow systems," *Anal Bioanal Chem*, vol. 376, 2003, pp. 1098-1103.

Shobha Jawaheer, "Development of a common biosensor formal for an enzyme based biosensor array to monitor fruit quality," *Biosensors and Bioelectronics*, vol. 18, 2003, 1429-1437.

M.D. Rubianes et al., "Amperometric Biosensor for Phenols and Catechols Based on Iridium-Polyphenol Oxidase-Modified Carbon Paste," *Electroanalysis*, vol. 12, No. 14, 2000, pp. 1159-1162.

"Redefining Electrochemical Measurement," available via the Internet at http://www.gamry.com/App_Notes/potentiostat_primer.htm, Gamry Instruments, Copyright 1997-04, pp. 1-5.

Rege, et al., "Enzyme-Polymer Single Walled Carbon Nanotube Composites as Biocatalytic Flims," Nano Letters Apr. 2003, vol. 3, No. 6, pp. 829-832.

Martel, et al., "Single-and multi-wall carbon nanotube field-effect transistors," Applied Physics Letters Oct. 1998, vol. 73, No. 17, pp. 2447-2449.

Xu et al. "An Amperometric Biosensor Based on the Coimmobilization of Horseradish Peroxidase and Methylene Blue on a Carbon Nanotubes Modified Electrode," Electroanalysis 2003, 15, No. 3, pp. 219-224.

Xue et al. "Single-wall Carbon nanotubes as Immobilization Material for Glucose Biosensor," Synthetic Metals 135-136 (2003) 831-832, pp. 2-3.

Office Action received in International Japanese Application No. 2006-544124, mailed May 26, 2009, 3 pages.

* cited by examiner

STEP 1: APPLY SENSOR ELEMENT E TO SUBSTRATE SURFACE

STEP 2: APPLY CNT FILM ON TOP OF SENSOR ELEMENT

STEP 3: EVAPORATE METAL CONTACTS TO COMPLETE CONDUCTION PATH ACROSS DEVICE

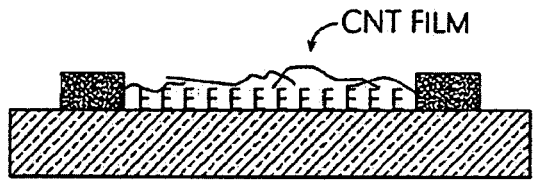

Fig. 10

STEP 1: CREATE CONDUCTING CNT ARRAY ON SUBSTRATE

STEP 2: CONCURRENT ELECTROCHEMICAL POLYMERIZATION OF POLYMER AND SENSING ELEMENT, E DIRECTLY ONTO CNTS COATING SUBSTRATE

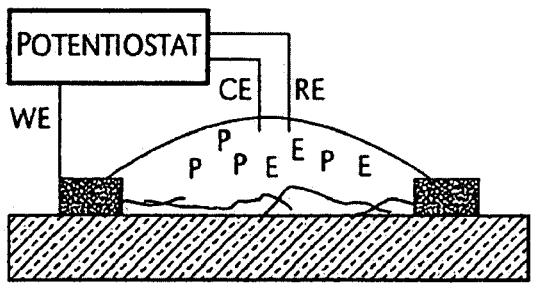

FINAL SCHEMATIC SHOWING SENSOR EMBEDDED IN POLYMER COATED CNT FILM

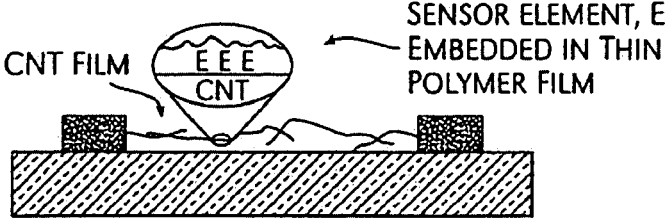

Fig. 11

NANOBIOSENSOR AND CARBON NANOTUBE THIN FILM TRANSISTORS

CROSS-REFERENCE TO RELATED APPLICATIONS

This application is a continuation of U.S. application Ser. No. 10/952,669 filed on Sep. 29, 2004, now U.S. Pat. No. 7,399,400 currently allowed, which claims priority to U.S. Provisional Application Ser. No. 60/507,436 filed Sep. 30, 2003 and U.S. Provisional Application Ser. No. 60/598,293 filed Aug. 3, 2004. This application is also related to U.S. application Ser. No. 11/011,645 filed Dec. 14, 2004.

TECHNICAL FIELD

The present invention relates in generally to systems and methods for chemical and biological detection, and more specifically to systems and methods of detecting chemical and biological analytes in various phases utilizing nanotubes.

BACKGROUND INFORMATION

Nanobiosensor

Biosensors are devices, which incorporate a biological element (e.g., enzyme, antibody) to detect chemical, biological and organic species. Biosensors have potential applications including, but not limited to, extreme environments (Dong et al., Electroanalysis, 15, 157, 2003), detection of food and pathogenic bacteria (Ivnitski et al., Electroanalysis, 12, 317, 2000), glucose monitoring (Wang, Electroanalysis 13, 983, 2001) and the food industry.

Conventional sensing electrodes (e.g., gold, platinum, glass, carbon) that have been used to immobilize biological enzymes have shown limited sensitivity and selectivity. In addition, sensor performance has been limited due to possible interfering compounds.

Most electrochemical biosensors operate in the liquid phase. There are instances where the analyte may be in the gaseous form and the electrochemical biosensor would be unable to detect the gaseous species. The performance of the liquid electrolyte sensors are limited by saturation of the analyte in the liquid phase, electrode corrosion and other operation problems including the requirement of continuous stirring to ensure the effective interaction of the analyte with the sensing element.

Aligned carbon nanotubes grown in situ are useful in electrochemical biosensing applications but the difficulties in achieving reproducibility severely limits their use in such applications. High manufacturing costs associated with producing aligned nanotubes further limit their commercialization.

There have been previous reports of electrochemical gas biosensors using ionic conducting films like nafion and tetrabutylammonium toluene-4-sulphonate (TBATS) for the detection of hydrogen peroxide and phenol vapors (Saini et al., Biosensors and Bioelectronics 10, 945, 1995; EP0585113A2), which use specific enzymatic reactions. However, these sensors used an enzyme (horseradish peroxidase) and a mediator (potassium hexacyanoferrate (II)) for sensing hydrogen peroxide with enzyme mediator gels. The "drop and dry" process of the mediator, gel and enzymes did not yield a high sensitive and selective detection. There have been reports about biosensors using a thick film electrochemical device with an insulating substrate for the determination of ethanol vapors using alcohol dehydrogenase enzyme which also involved the "drop and dry" process (EP634488A2).

CNT-TFT

Chemical sensors are devices that detect chemical and biological species based upon an interaction between two molecules. These sensors can be used to detect various analytes in gas, liquid and solid phases. Sensors can be manufactured to operate in ambient or extreme environmental conditions. When optimized, chemical sensors can detect very low levels of a desired analyte, however, the drawback is usually the large amount of support equipment. This equipment usually prevents the sensors from being portable.

Conventional sensors can be made using a wide variety of techniques, each specific to the desired detectable analyte. A suitable technique would focus on the interactions between two molecules that result in signal generation. The signal produced could be light emission, electron transfer or other physical change. Every sensor needs a method of transduction, i.e., converting the chemical event to a measurable output signal.

Current methods of detection have limited selectivity when operating at the limits of detection. At these extremes of performance, separating a signal from the surrounding noise becomes extremely difficult. One method for increasing this signal to noise ratio is to have internal amplification of the desired signal. Internal amplification prevents additional noise being introduced into a detection system through outside electronics. A simple way to achieve amplification is to build the detector using transistor architecture. This architecture can take advantage of the inherent gain associated with a semiconducting material.

Carbon nanotube (CNT) transistors have been known for several years. (Tan et al., Nature, 1998 (393) 49, Martel et al., Appl. Phys. Lett. 1998 (73) 2447). Many examples of these devices rely on a single CNT placed between electrodes. These devices are difficult to prepare, requiring tedious placement of electrodes with respect to CNT position. These are advanced techniques that require highly specialized instrumentation including electron microscopes and electron beam writing. The use of this instrumentation required for characterization and fabrication prevents this from being a manufacturable technique.

SUMMARY OF INVENTION

An embodiment of the invention is a sensor for detecting an analyte comprising: a carbon nanotube; a polymer immobilized to the carbon nanotube; and a sensing element for detecting the analyte, wherein the sensing element is immobilized to the carbon nanotube.

Another embodiment of the invention is a sensor for detecting an analyte comprising: a carbon nanotube; a polymer immobilized to the carbon nanotube; and a sensing element for detecting the analyte, wherein the sensing element is immobilized to the polymer.

Another embodiment of the invention is a sensor comprising a sensing element for detecting an analyte embedded in a polymer matrix interdispersed with carbon nanotubes.

Another embodiment of the invention is a sensor comprising a sensing element for detecting an analyte, wherein the sensor is coupled to a carbon nanotube.

Yet another embodiment of the inventions is a method of detecting an analyte comprising the steps of: immobilizing a polymer and sensing element to a carbon nanotube; and utilizing a transduction mechanism with the sensing element to detect the analyte.

BRIEF DESCRIPTION OF DRAWINGS

For a more complete understanding of the present invention, and the advantages thereof, reference is now made to the following descriptions taken in conjunction with the accompanying drawings, in which:

FIG. 10 depicts a schematic showing creation of a CNT-TFT on a sensing substrate;

FIG. 11 depicts a schematic of electropolymerizing sensing element, E, and polymer host onto CNT-TFT architecture; working element or electrode (WE), control element or electrode (CE), and reference electrode (RE);

DETAILED DESCRIPTION OF THE INVENTION

Figure 1:
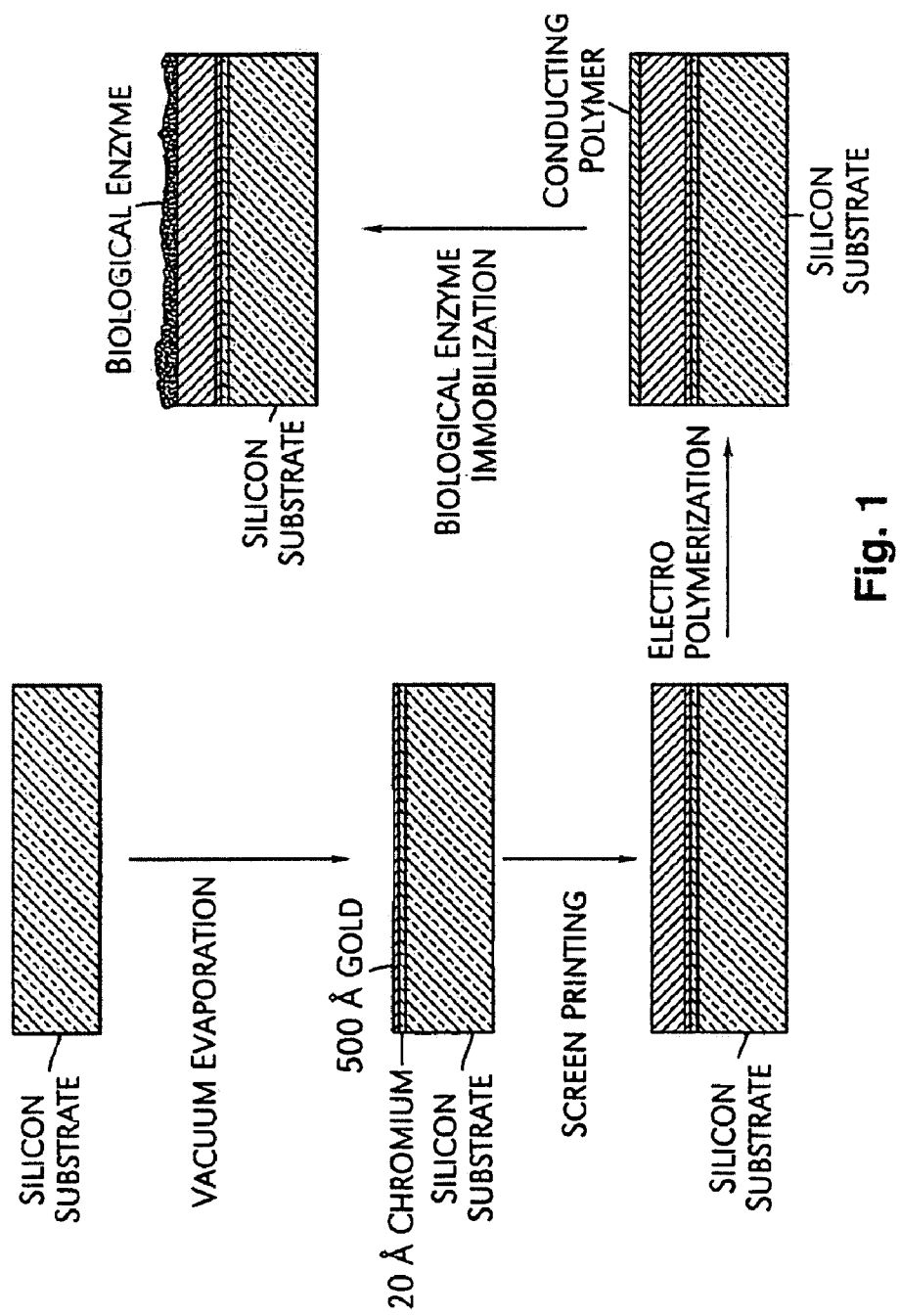
FIG. 1 depicts a schematic showing the formation of the enzyme electrode.
Figure 2:
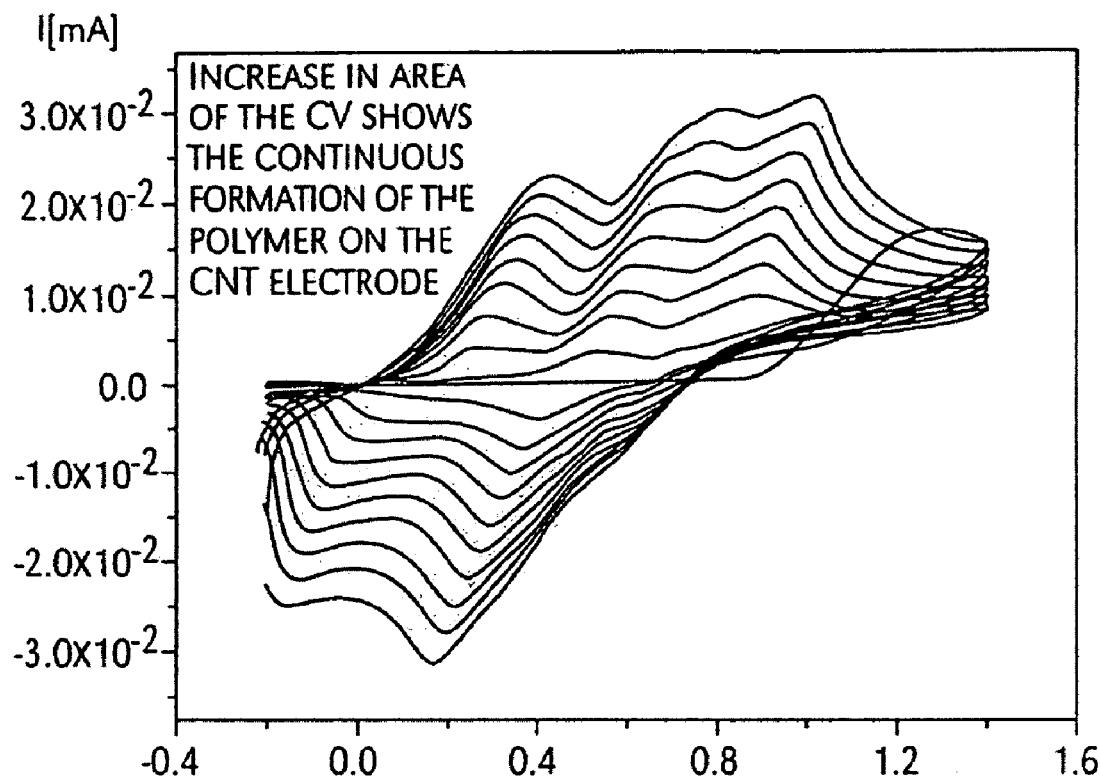
FIG. 2 depicts a cyclic voltammogram showing the polymerization of aniline (conducting polymer) onto the carbon nanotube electrode; scan rate=50 mV/s.

The present invention is directed to systems and methods for detecting chemical, organic and biological analytes.

While most of the terms used herein will be recognizable to those of skill in the art, the following definitions are nevertheless put forth to aid in the understanding of the present invention. It should be understood, however, that when not explicitly defined, terms should be interpreted as adopting a meaning presently accepted by those of skill in the art.

"Analyte," as defined herein, refers to the substance being measured in an analytical procedure.

"Carbon nanotubes," as defined herein, refers to sheets of graphite that form tubes.

"Chemical sensor," as defined herein, refers to devices that detect chemical and biological species based upon an interaction between two molecules.

"Immobilized" as defined herein, refers to a substance being attached, directly or indirectly (e.g., through a polymer), to another substance.

"Multi-walled nanotube," as defined herein, refers to nanotubes within nanotubes.

"Nanotube," as defined herein, refers to any tube with nanoscale dimensions.

"Sensing element," as defined herein, refers to material responsible for the detection of the substance of interest.

"Sensor," as defined herein, refers to a system or device that measures or detects a substance.

"Single-walled nanotube," as defined herein, refers to a nanotube that does not contain another nanotube.

"Thin film transistor," as defined herein, refers to thin films deposited for metallic contacts.

The present invention incorporates a number of advantages over presently known devices, systems or processes. These advantages include:

- The present invention provides a sensing method that is not affected by common interfering compounds. The high surface ratio and three dimensional network of the nanoscale composites tend to lower the oxidation potential of compounds generated as a result of reaction between the analyte and the biological enzymes. This helps to eliminate the interference from other oxidizable species in biochemical reactions.
- The present invention provides a polymer that can be chosen to be inert to certain chemical environments. This would make it possible to operate the sensor in hazardous conditions, such as caustic and acidic systems, where most sensors would break down.
- The present invention provides alternative methods to prepare carbon nanotube electrodes for electrochemical sensing which eliminates the cumbersome procedure of aligning carbon nanotubes.
- The present invention provides a method for immobilizing biological enzymes and polymers in situ onto the carbon nanotubes to develop highly selective and sensitive biosensors.
- The present invention provides an effective way to sense gases through the electrochemical sensing mechanism by the employment of a gas permeable membrane.

Nanobiosensor

The inventors have developed nanoscale composites of polymers (e.g., polyaniline, polypyrrole) and carbon nanotubes for electrochemical sensing applications. For example, the conducting polymer acts as the electron mediator while the carbon nanotubes provide enhanced surface area. The inventors have also immobilized an enzyme onto these structures through electrochemical polymerization to mediate a biological reaction specific to a desired analyte. The nanoscale composites of carbon nanotubes and conducting polymers promote enhanced electron transfer for the biochemical reactions. This yields higher sensitivity and selectivity compared to conventional sensing electrodes. The high surface ratio and three dimensional network of these composites tend to lower the oxidation potential of compounds generated as a result of reaction between the analyte and the biological enzymes. This helps to eliminate the interference from other oxidizable species in biochemical reactions. The inventors have also devised a simple method of preparing carbon nanotube electrodes for electrochemical sensing by screen printing and spraying methods which are feasible for device fabrication. This invention provides an easy and effective method towards the commercialization of carbon nanotube biosensors.

An embodiment of the present invention is a biosensor for detecting an analyte comprising a carbon nanotube, a polymer and a biological element attached to the nanotube to form an active sensing element. The polymer and the biological element can also be attached in situ to the nanotube to form the sensing element. The carbon nanotube can be used as an electrode in an electrochemical, TFT (thin film transistor), enzyme FET (field effect transistor) or other transduction mechanisms to detect analytes using a specific chemical or biological reaction schemes The polymer can be comprised of a conjugated, redox, insulating or conducting polymer or of a similar kind that provides a mechanical support and/or promotes electron transfer, a recognition event between the analyte and the sensing element. The conducting polymer can comprise of polyaniline, polypyrrole, polythiophenes and substituted derivatives of these polymers etc.

The biological element can be an enzyme, antibody, nucleic acid or other biologically active entity. The enzyme may be a member of a group including, but not limited to, Oxidoreductases, Transferases, Hydrolases, Lyases, Isomerases, Ligases, Dehydrogenases, Glycosidases, Kinases, Luciferases, Lysing Enzymes, Oxidases, Proteases, and their substituents.

In an embodiment of the invention, the inventors have incorporated a membrane that is permeable to gaseous species into the electrochemical sensing mechanisms in order to sense gaseous compounds. Any gas which can undergo an electrochemical reaction with the sensing electrode can be sensed effectively.

This invention may be used in sensing gases and liquids that can undergo an electrochemical reaction at the sensing electrode. This invention can be used for, but not limited to, the detection of hydrogen peroxide, which undergoes the following reaction in the electrolytic cell.

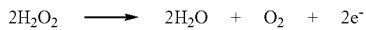

Figure 4:
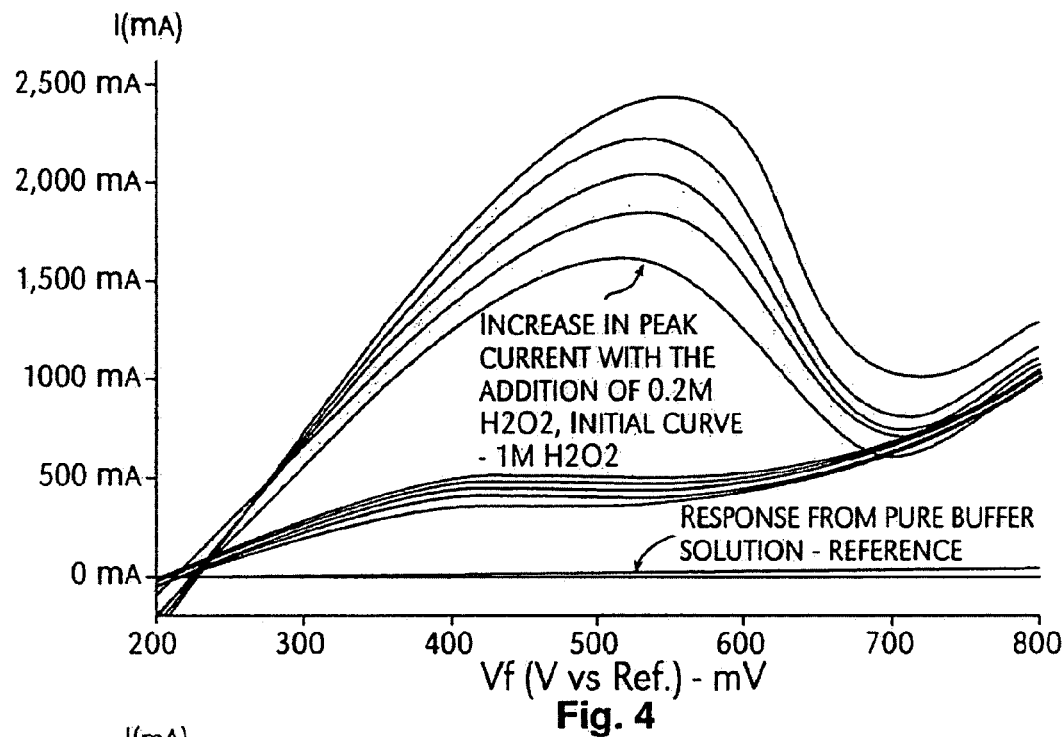
FIG. 4 depicts a cyclic voltammogram showing the increase in the amperometric oxidation with the successive addition of 0.2M $H_2O_2$ in the 1M $H_2O_2$; also shown is the response without hydrogen peroxide.

The electrolytic cell consists of a working electrode (carbon nanotubes) where the oxidation of hydrogen peroxide occurs. The cell also consists of a counter electrode (e.g., platinum wire), which counters the reaction in the working electrode (reduction) and a reference electrode (e.g., standard calomel electrode, SCE). The electrolytic reaction produces electrons which can be read by a current response at a characteristic potential. The characteristic potential represents the oxidation potential of the analyte (e.g., hydrogen peroxide). This current will produce an amperometric oxidation peak in a cyclic voltammogram. When the concentration of the analyte (e.g., hydrogen peroxide) is increased, there is a corresponding increase in the peak current (FIG. 4).

In another embodiment, the enzyme glucose oxidase is immobilized into the sensing electrode along with the conducting polymer to sense glucose in the solution based on the following electrochemical reaction.

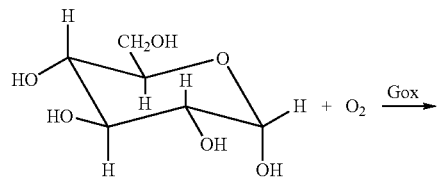

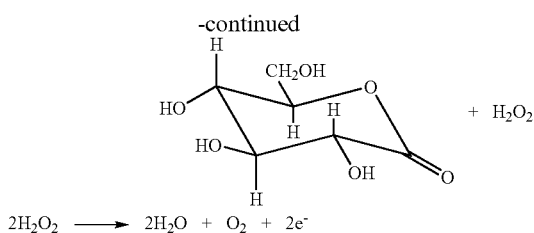

Glucose is oxidized to form hydrogen peroxide, which can be sensed by the amperometric oxidation peak at a characteristic potential. An main advantage of employing carbon nanotubes in the sensing process is that the oxidation of hydrogen peroxide is lowered to a range of 0.3 V to 0.45 V (depending on the nature of nanotubes). This eliminates interference by compounds such as ascorbic acid, urea, uric acid, acetametaphenone etc. which oxidize around 0.6 V. The conventional electrodes (e.g., gold, platinum) have an oxidation potential of 0.6 V wherein the characteristic peak is influenced by the interfering compounds. The carbon nanotube sensor also provides enhanced sensitivity due to higher surface area in comparison to the conventional electrodes sensing electrodes (e.g., gold, platinum).

Figure 5:
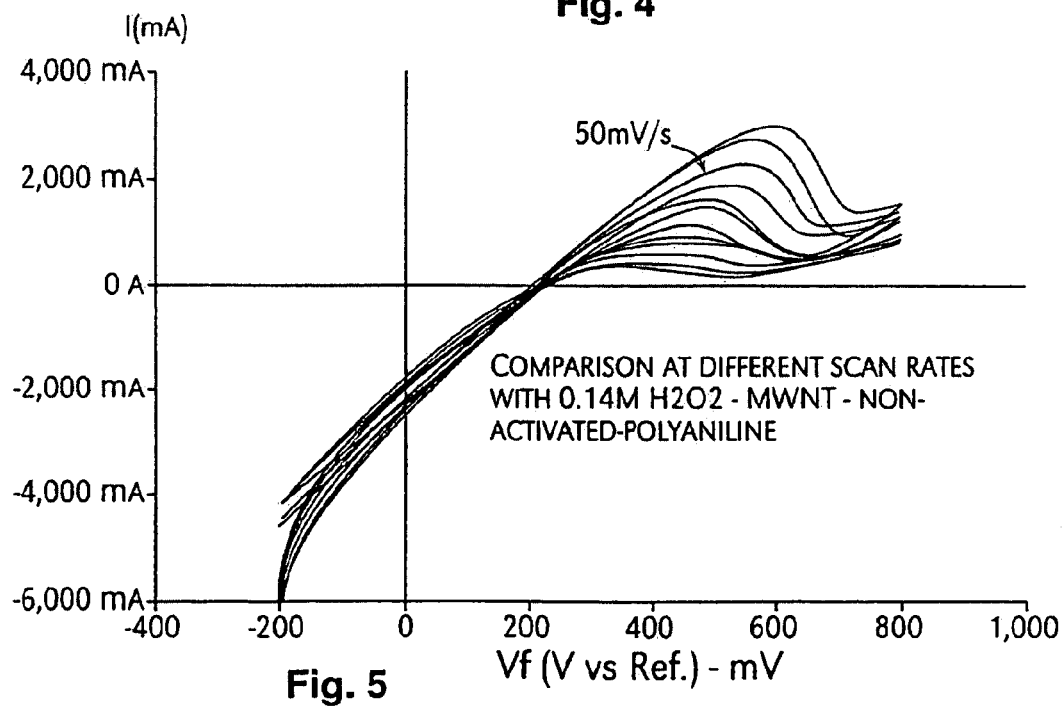
FIG. 5 depicts a cyclic voltammogram showing the increase in the amperometric oxidation peaks with the increasing scan rates (5 mV/s is the lowest and 125 m V/s is the highest)

The present invention also improves the operation of the sensor in a wide range of scan rates as shown in FIG. 5. The optimum scan rate for all the electrochemical sensing measurements was optimized to be 50 mV/s.

Figure 6:
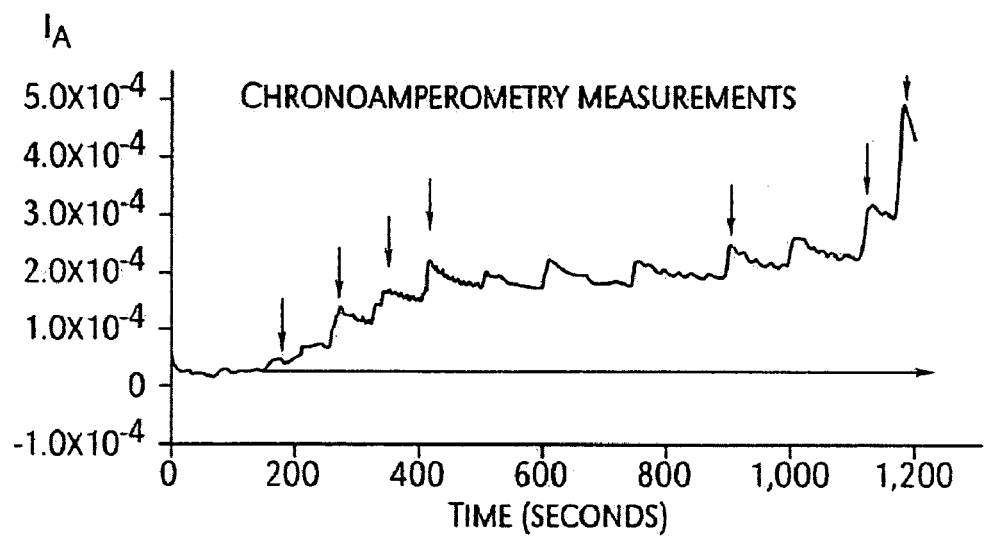
FIG. 6 depicts a chronoamperometric response of the MWNT spray sensor with successive additions of hydrogen peroxide (shown by arrows)
Figure 7:
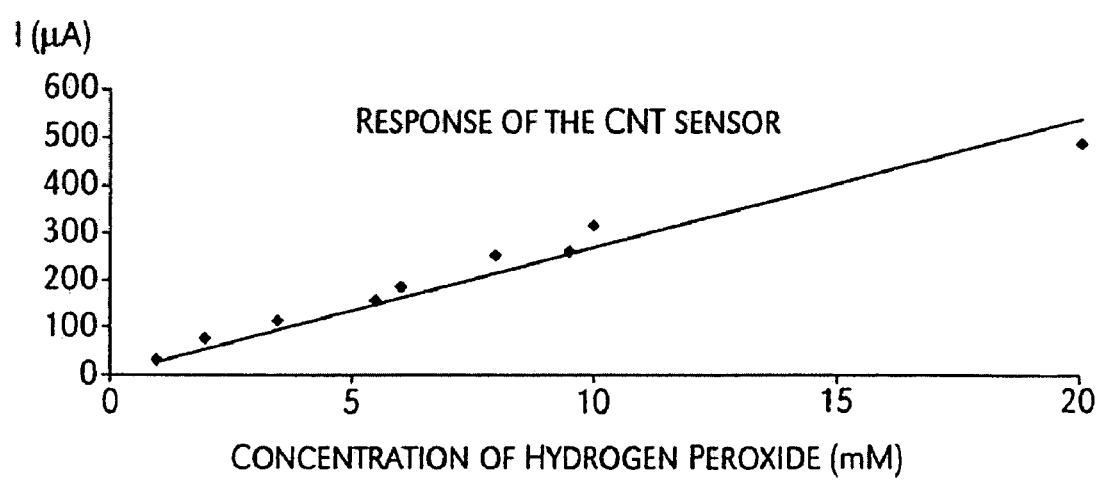
FIG. 7 depicts a response of the MWNT spray sensor to varying concentrations of hydrogen peroxide.

The present invention also provides an effective way to determine wide ranges of concentration of gases and liquids electrochemically. FIG. 6 depicts the chronoamperometric response of the sensor to hydrogen peroxide liquid at a fixed characteristic potential of 0.3 V. The current response increases with addition of the analyte, hydrogen peroxide. The response of the sensor is linear over very small concentrations (<30 mM) (FIG. 7). This is the general concentration of glucose level in human blood (Yasuzawa and Kunugi, Electrochem Commun., 1, 459, 1999). The present invention provides an easy and effective way for glucose sensing.

Figure 8:
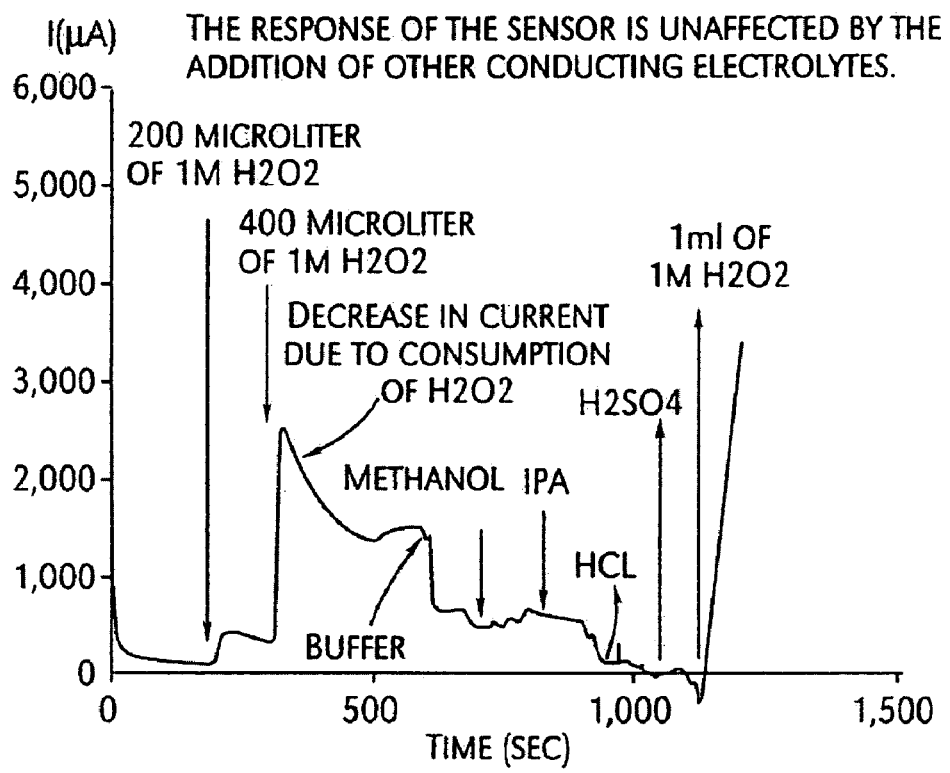
FIG. 8 depicts a chronoamperometric response of the MWNT spay sensor with successive additions of different compounds (shown by arrows)

The present invention also provides a sensing mechanism which is not affected by interfering compounds. The response of the hydrogen peroxide sensor is unaffected by the addition of other conducting electrolytes like, potassium phosphate buffer, methanol, isopropyl alcohol, sulfuric acid, hydrochloric acid (FIG. 8). The sensor is highly selective to hydrogen peroxide at the characteristic potential (0.3 V). Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Table 1 shows a comparison of different nanotube electrodes for electrochemical sensing applications. The sensitivity of different nanotube electrodes has been determined. The multi-walled nanotube (MWNT) spray electrode has around three times higher sensitivity as the aligned carbon nanotubes prepared by the chemical vapor deposition method, which are desired for sensing applications. Generally, the multi-walled nanotube electrodes (MWNT) were found to be better candidates for electrochemical sensing in comparison with the single walled nanotubes (SWNT). The firing and activation process removed around 40% nanotubes from the substrate which decreased the sensitivity of the biosensor.

Previous efforts of using carbon nanotube paste electrodes for biosensing did not yield good sensitivity due to the insulating components like mineral oil (Rubianes and Rivas, Electrochemistry Communications, 5, 689, 2003) and prussian blue (Ricci et al., Analytical Letters, 36, 1921, 2003) that were used to bind the nanotubes. The present invention utilizes a conducting matrix for enzyme immobilization. Analytes and enzymes that may be used in the present invention include but are not limited to those listed in Table 2.

TABLE 1

| Electrodes | Sensitivity (mA/ M·cm$^2$) | Peak current (mA) | Oxidation potential [Volts] | Area (cm$^2$) | Tested solution (M) |
|---|---|---|---|---|---|
| Aligned MWNT-PPY | 70.88 | 0.638 | 0.450 | 0.09 | 0.1 M H$_2$O$_2$ |
| Aligned MWNT-PANI | 893.61 | 0.525 | 0.4625 | 0.25 | 2.35 mM Glucose |
| MWNT spray-PANI | 2857 | 3.2 | 0.302 | 0.56 | 2 mM H$_2$O$_2$ |
| Paste Electrodes with polymer MWNT (13%) | 6 | 1.5 | 0.55 | 0.25 | 1 M H$_2$O$_2$ |
| MWNT (50%) | 842.8 | 0.421 | 0.216 | 0.5 | 1 mM |

TABLE 2

| Analyte | Enzyme |
|---|---|
| Glucose | Glucose oxidase, Glucose dehydrogenase |
| L-Lactate | Lactate oxidase, Lactate dehydrogenase |
| Phenol, Catechol, p-cresol, m-cresol, Atrazine | Tryosinase (polyphenol oxidase) |
| Urea | Urease |
| Ascorbic acid | Ascorbic oxidase |
| Choloestrol | Choloestrol oxidase, Choloestrol dehydrogenase |
| Fructose | Fructose dehydrogenase |
| Lipids, Triglycerides | Lipase |
| Uric acid | Uricase |
| Choline, Lecithin | Choline oxidase |
| Hemoglobin | Pepsin |
| Glutamate | Glutamate oxidase |
| Alcohol | Alcohol dehydrogenase, Alcohol oxidase |
| Carbon monoxide | Carbon monoxide dehydrogenase |
| Sucrose | Invertase, mutarose |
| Malate | Malate oxidase, NADH oxidase |
| Lycine | Lycine oxidase |
| Glycerol | Glycerol dehydrogenase |
| Citrate and pyruvic acid | Citrate lyase and pyruvate oxidase |
| Sulphite | Sulphite oxidase |
| Gelatinized starch | Amyloglucosidase, α-amylase, glucose oxidase |
| Penicillin | Immobilized penicillin acylase |
| Organo phosphorous pesticides | Butyrilcholine esterase, choline oxidase |
| Fish freshness (biogenic amines) | Diamine oxidase, amyloglucose oxidase |
| Tannin | Laccase |
| Formate | Formate dehydrogenase |
| Hydrogen peroxide | Horseradish peroxidase |

The polymers utilized may include, but are not limited to, insulating, conducting, or redox polymers. Insulating polymers are used for mechanical support when immobilizing enzymes. The conjugated and conducting conjugated polymers are used as electron mediators. The redox polymers are used to promote reduction—oxidation reactions between the analyte and the sensing element. The polymers used may include, but are not limited to any one or more of the following; polyaniline, polypyrrole, polythiophenes and substituted derivatives of these polymers.

A multitude of biological elements may be used to detect a wide variety of analytes in addition to those listed in Table 2. Enzymes that may be used include but are not limited to, the classes Oxidoreductases, Transferases, Hydrolases, Lyases, Isomerases, Ligases, Dehydrogenases, Glycosidases, Kinases, Luciferases, Lysing Enzymes, Oxidases, Proteases, and their substituents.

Antibodies (e.g. immunoglobulins, recombinant antibodies, monoclonal antibodies) may be immobilized with the conducting polymer on the carbon nanotube to detect a corresponding antigen in the analyte through a specific antigen-antibody interaction.

A DNA hybridization event may be detected by immobilizing a single stranded DNA onto the conducting polymer—carbon nanotube system and recording the hybridization event with the analyte.

The signal from the biological/chemical interaction between the analyte and the sensing element can be recorded using electrochemical techniques (amperometric, potentiometric etc.), using a thin film transistor (TFT) or enzyme field effect transistor (FET) technique based on the nature of application.

This invention also provides a simple and effective way to sense gases which can undergo an electrochemical reaction. Some examples include, but are not limited to, the electrochemical sensing using this invention are:

Carbon monoxide (CO): $CO + H_2O \rightarrow CO_2 + 2H^+ + 2e^-$

Hydrogen Sulphide (H$_2$S): $H_2S + 4H_2O \rightarrow H_2SO_4 + 8H^+ + 8e^-$

Sulphur Dioxide (SO$_2$): $SO_2 + 2H_2O \rightarrow H_2SO_4 + 2H^+ + 2e^-$

Nitric Oxide (NO): $NO + 2H_2O \rightarrow HNO_3 + 3H^+ + 3e^-$

Nitrogen Dioxide (NO$_2$): $NO_2 + 2H^+ + 2e^- \rightarrow NO + H_2O$

Hydrogen (H$_2$): $H_2 \rightarrow 2H^+ + 2e^-$

Chlorine (Cl$_2$): $Cl_2 + 2H^+ + 2e^- \rightarrow 2HCl$

Hydrogen Cyanide (HCN): $2HCN + Au \rightarrow HAu(CN)_2 + H^+ + e^-$

Figure 3:
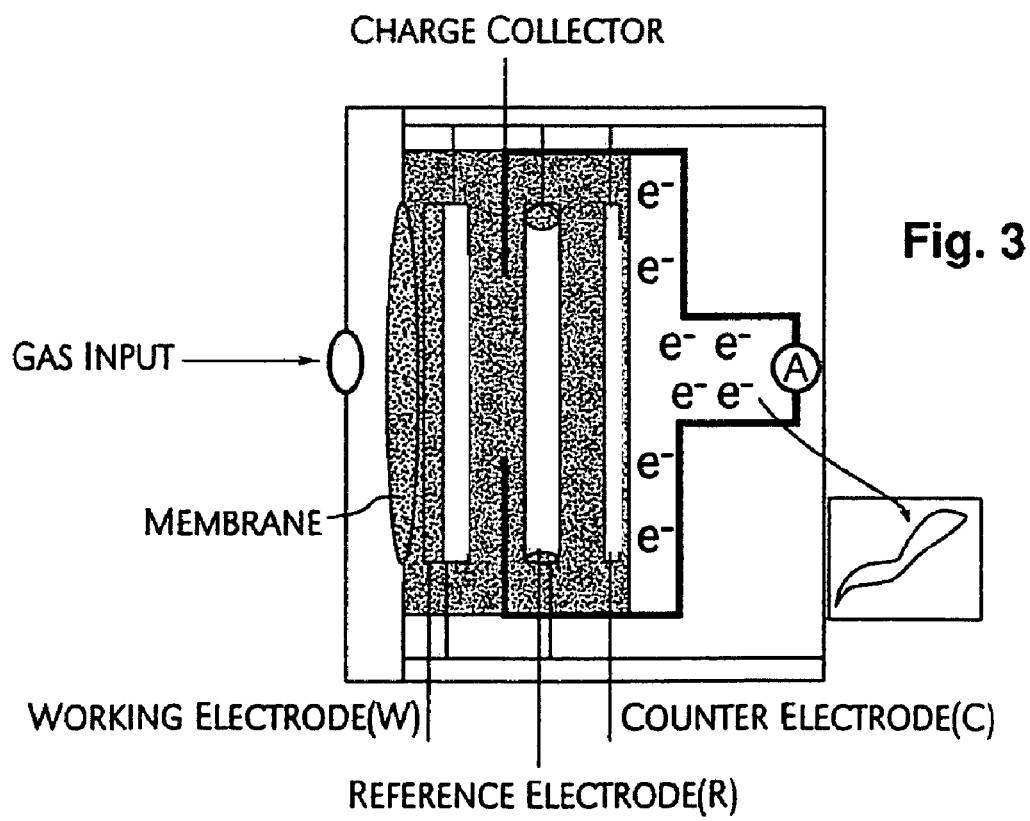
FIG. 3 is a depiction of an embodiment of the nanobiosensor.

Ethylene Oxide (C$_2$H$_4$O): $C_2H_4O + 2H_2O \rightarrow C_2H_4O_3 + 4H^+ + 4e^-$ Ammonia (NH$_3$): $12NH_3 + I_2 + 6H_2O \rightarrow 2IO_3^- + 12NH_4^+ + 10e^-$ A hydrophobic gas permeable membrane was employed for the detection of gases through this invention. Fluoropolymers such as polytetrafluoroethylene (PTFE), trifluorinatedethylene (TFE) and fluorinated ethylene propylene (FEP) have very low gas absorption properties and are suitable for use in this invention. It is foreseen that any fluoropolymer with a low gas absorption property would be suitable for use in the present invention. The membrane (2) may be encapsulated near the working electrode (3) as shown in FIG. 3. In FIG. 3, the analyte may be detected due to a chemical/biological reaction with the sensing element in the working electrode (3) in a typical electrochemical transduction scheme comprising of an electrolyte (1), reference electrode (4) and the counter electrode (5). The electrons generated as a result of the electrochemical reaction between the gas and the sensing element can be carried out by a charge collector (6) and can be linked to an ammeter or a light emitting diode (LED) to indicate the presence of the desired analyte.

This invention provides a method to detect hydrogen peroxide at lower anodic potentials (0.2 to 0.4 V) which eliminates the interference from other compounds like ascorbic acid, acetametaphenone, urea, uric acid which oxidize at 0.6-0.8 V.

In addition to electrochemical techniques, CNT based sensors may also be created utilizing a thin-film transistor technique. (Snow et al., App. Phys. Lett., 2003, 82 (13) 2145). This technique allows CNT films to be applied to a substrate independent of their position. It relies on low resistance tunnel junctions between intersecting CNTs to establish a sub-monolayer conducting film. This film can be patterned and is completely compatible with existing microelectronic processing techniques.

This thin-film transistor technique does not require a completely semiconducting CNT material. It relies on percolation pathways where the semiconducting CNTs in the mixture form the current limiting connections. This is in contrast to a single CNT device. If the single CNT is not semiconducting, the transistor will not work. At present, there are no methods for controlling the electronic structure while producing CNTs. This means that a statistical distribution of metallic and semiconducting CNTs will be present. The device yield for an individual CNT device will be, at a maximum, the percentage of semiconducting CNTs in the sample. At present this is nearly 60%.

The inventors have developed a nanoscale architecture for chemical sensing. This architecture uses carbon nanotube based thin-film transistors to provide amplification of signal for chemical sensors. The chemical sensor may have several forms depending on the desired application and intended results.

The invention is based on a combination of polymer coatings, specific chemical binders, and a carbon nanotube thin film transistor (CNT-TFT) device. Polymers may be used as a conductive pathway and/or a mechanical support for hosting the active chemical sensing element. The polymer may be applied using various techniques, including but not limited to, spin coating, electropolymerization, chemical vapor polymerization or printing techniques (i.e. ink jet printing). The polymer may be electro-polymerized in place. Insulating polymers may be used to support a sensing element (labeled "E" in the drawings), bypassing the need for direct chemical attachment to the TFT surface. These polymers may also be used to define specificity by allowing or excluding diffusion of analyte molecules.

The process of making the CNT-TFTs utilizes liquid deposition processes. These processes allow for manufacturing of large area substrates (>1 m$^2$) and on rigid or flexible substrates, such as glass or plastics.

Figure 9:
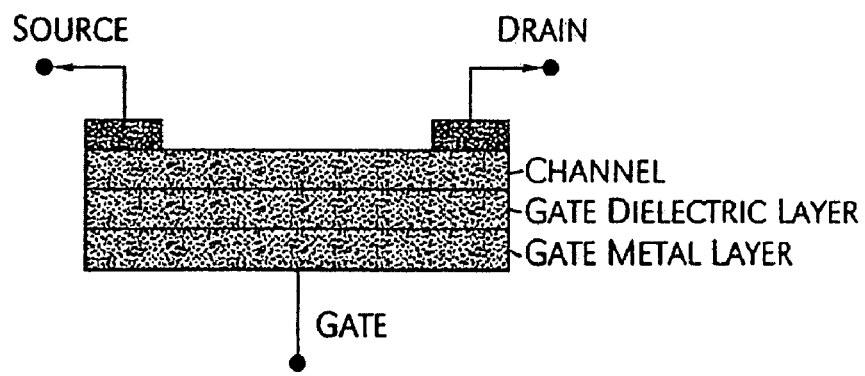
FIG. 9 depicts a basic structure of a thin-film transistor.

A gated TFT structure is depicted in FIG. 9. FIG. 9 depicts the concept of using a gate voltage to control the conduction of a channel layer. The resistance of the channel layer between the Source and the Drain is controlled by the voltage on the Gate Metal Layer. The gate dielectric layer can be $SiO^2$, SiNx or SiOxNy, or other insulating material. Slight changes in the gate voltage can make dramatic changes in the conductivity of the channel layer. Any nanotube structure would be suitable for use in the present invention. Nanotube structures that may be used include but are not limited to single-wall nanotubes and multi-wall nanotubes. Other structures than that depicted in FIG. 9 are foreseen to be suitable in the present invention.

In one embodiment of the CNT-TFT sensor, the sensing element (E) is attached directly to the gate dielectric layer. The CNT film is then deposited onto this surface (FIG. 10). When an analyte binds with E, the new compound creates a change in conductivity of the TFT. This change in conductivity is due to a change in carrier concentration due to an electron transfer in the locality of the CNT, electron transfer between the element (E) and the CNT, or a physical size change from the binding changing the interconnection between adjacent CNTs. Because these CNT-TFTs are semiconducting, a small change in carrier concentration results in large changes in current through the devices. This structure then becomes a sensor for the analyte that binds to the sensing element (E).

In another embodiment of the sensor, the sensing element (E) and polymer are attached to CNT's already on the surface. This can be a direct attachment or direct host in a polymer. The polymer can be used to enhance the sensitivity of the sensor or facilitate signal transfer to the CNTs. This polymer can be deposited using electrochemical polymerization (FIG. 11), or through spin and spray coating of a polymer solution.

Figure 12:
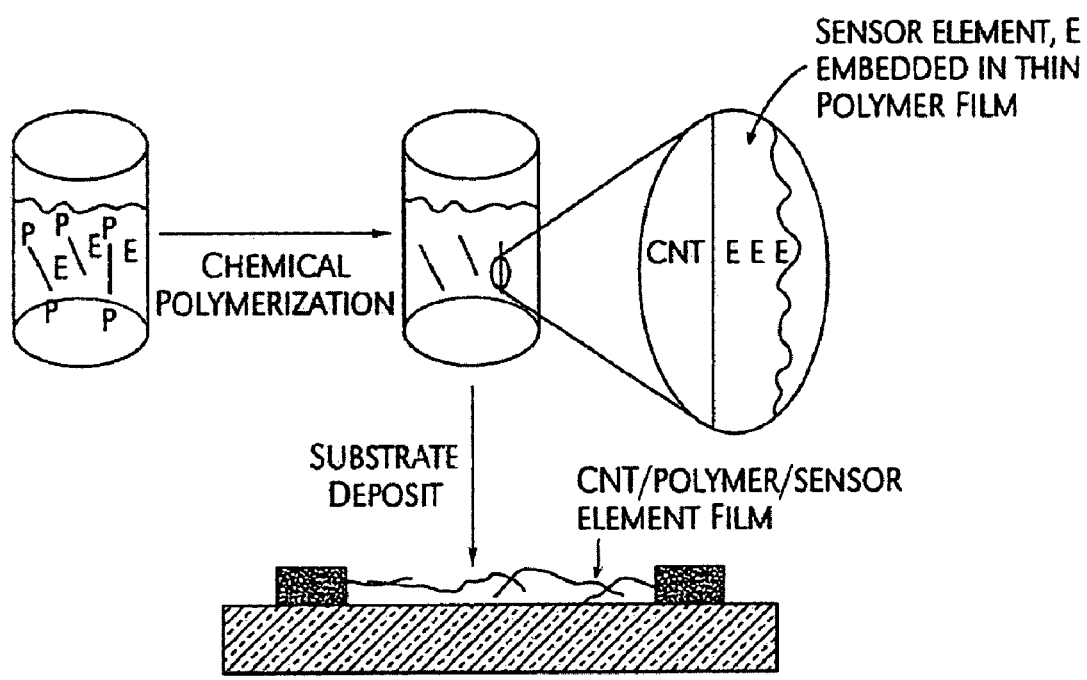
FIG. 12 depicts a schematic showing solution based deposition of sensor coated CNTs.
Figure 13:
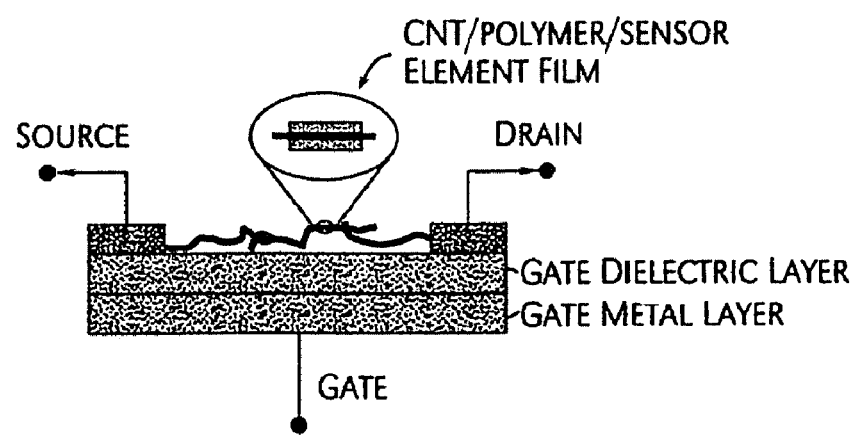
FIG. 13 depicts a schematic of showing solution-based deposition of sensor coated CNT on a standard TFT structure.

In another example of the sensor, the sensing element (E) and support polymer are attached directly to the CNTs in solution. This can be facilitated through a chemical reduction of the polymer monomer concurrent in solution (FIG. 12). These polymer and sensor element coated CNTs are then deposited on the TFT substrate.

In another embodiment of the present invention, the CNTs are coated with the sensing element (E) or with a polymer with the sensing element (E) embedded in the polymer. The coated CNTs are deposited in a monolayer on a dielectric gate layer.

In yet another embodiment, the carbon nanotubes are coated onto a working electrode of an electrochemical cell (FIG. 3). The nanotubes are coated in the cell, the working electrode is removed and the carbon nanotubes are harvested from the electrode and dispersed onto the substrate.

Figure 14:
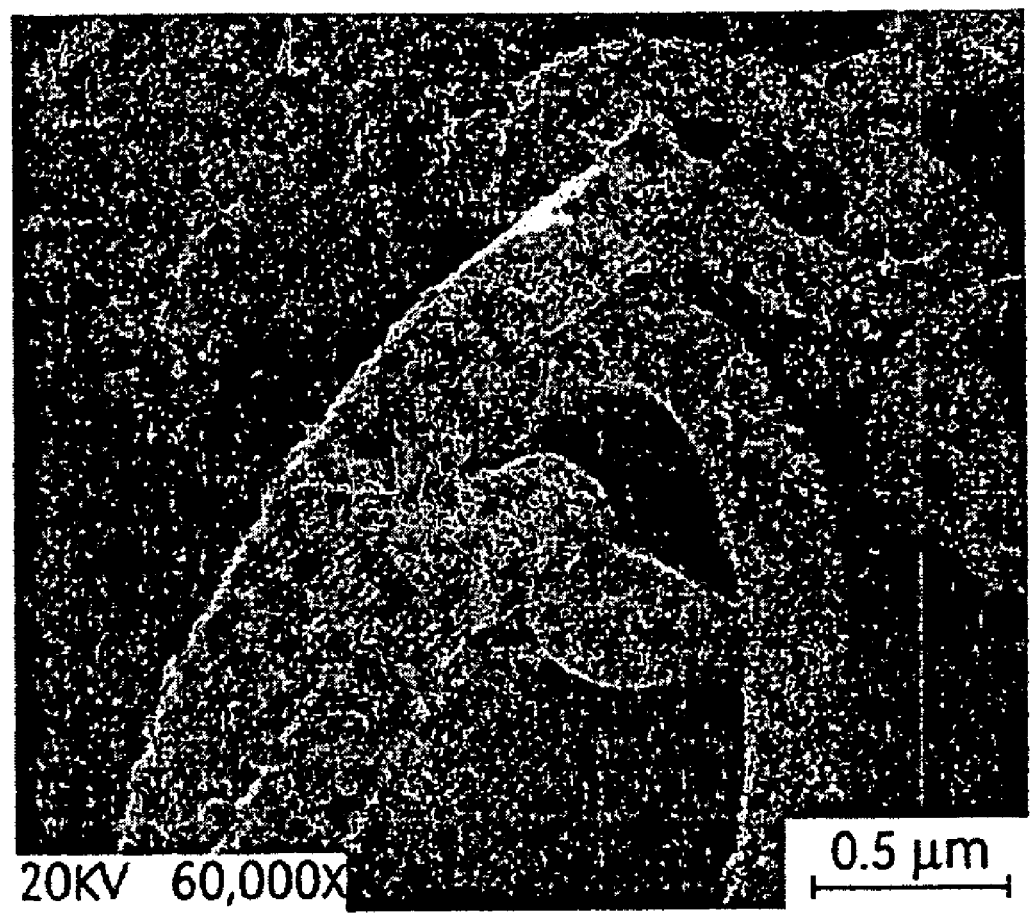
FIG. 14 depicts an image of a polymer-enzyme coated CNT.

An embodiment of the present invention in which a CNT is coated with a polymer that contains an example of an embedded sensing element (E) is shown in FIG. 14. Near the top of the image, a nanotube is protruding from the polymer film.

The devices described herein are used for chemical or biological sensing. The sensing element (E) is defined by the type of sensor to be created. If E is a biological enzyme, the sensor will be a nanobiosensor. A glucose sensor would be created if glucose oxidase were immobilized. For example, glucose oxidase will react with glucose to produce hydrogen peroxide, $H_2O_2$. The peroxide changes the chemical environment of the CNT through electron transfer. The electron transfer will effectively change the carrier concentration in the CNT film, thus gating ON or OFF the CNT-TFT. Devices can be designed with electron transfer into (donating) or out of (withdrawing) the CNT. Thus, the response is able to be tuned when combined with a p- or n-type transistor.

Devices are tested by measuring current, $I_d$, through the device at a given drain voltage, $V_d$. When a sensing event is detected, the current will change depending on the type of interaction and the nature of the transistor itself. For example, a p-type transistor will show a decrease in current when an electron withdrawing chemical event occurs, reducing the carrier concentration. The magnitude of current change is directly proportional to the number of analytes encountered by the sensor. The advantage of the TFT architecture is the ability to get orders of magnitude in current change from only a few analytes.

EXAMPLES

The following example is included to demonstrate particular embodiments of the present invention. It should be appreciated by those of skill in the art that the systems and methods disclosed in the example which follows merely represent exemplary embodiments of the present invention. However, those of skill in the art should, in light of the present disclosure, appreciate that many changes can be made in the specific embodiments described and still obtain a like or similar result without departing from the spirit and scope of the present invention.

These examples serve to illustrate certain exemplary embodiments of the present invention that comprise:

Example 1

Electrochemical Instrumentation and Materials

Instrumentation: Experiments using electro-polymerization were carried out using a three electrode Gamry (v. 4.02) electrochemical system coupled to a Gamry Potentiostat (PCI4/300). The three electrodes included a working, counter and Ag/AgCl reference. The measurements and analysis were performed and recorded using the Gamry Software (v. 1.02).

Materials: Single-walled carbon nanotubes (SWNTs) and multi-walled carbon nanotubes (MWNTs) may be purchased from any source. In the CNT-TFT, the SWNTs used have diameters that range from 1 to 3 nm and lengths that range from less than one micron to greater than 10 µm. SWNTs have been used "as-produced" (AP) or purified with similar results. This disclosure does not specify how the carbon nanotubes were made, although methods that deliver higher concentrations of semiconducting nanotubes may be used, either as produced or as a post-fabrication process procedure.

In the nanobiosensor, the multi-walled nanotubes had diameters 10-30 nm and lengths 1-10 µm. Single-wall carbon nanotubes (SWNT) used have diameters of 1-2 nm and lengths of 5-20 µm. Organic vehicle and glass frit were obtained from Daejoo Electronic Materials Co., Ltd, and thinner was obtained from Dupont Electronics Microcircuits Industries. Aniline, pyrrole, sulfuric acid, sodium perchlorate, glucose oxidase, hydrogen peroxide, and standard glucose solution were obtained from Aldrich.

Example 2

Preparation of Carbon Nanotube Electrodes

Carbon nanotube paste electrodes (0.5 cm$^2$) were prepared by mixing 50% by weight of carbon nanotubes with 43% by weight of organic vehicle and 7% by weight of glass frit in a mortar and pestle for 30 minutes followed by grinding in a three roll mill for 20 minutes to disperse the clusters in the mixture. The composite was then screen printed through a mask of known area onto a silicon substrate, vacuum evaporated with 20 angstroms chromium and 500 angstroms gold. The substrate was then baked at 100° C. for 10 minutes in an oven and cooled at room temperature as illustrated in FIG. 1. Different weight percentages of carbon nanotubes can also be employed for the electrode preparation. The prepared carbon nanotube paste electrodes may be fired (hard baked) to remove the organic vehicle and activated using a tape.

Carbon nanotube spray electrodes (0.5 cm$^2$) were prepared by dissolving a known quantity of carbon nanotubes (e.g., 0.1 g) in 20 ml isopropyl alcohol, followed by ultrasonication for 5 minutes and spraying the solution onto the substrate (silicon substrate, vacuum evaporated with 20 angstroms chromium and 500 angstroms gold). The spray electrode was then baked at 100° C. for 10 minutes in an oven and cooled at room temperature.

The carbon nanotubes can also be prepared by a chemical vapor deposition process comprising a catalyst (e.g., nickel, copper, cobalt, iron) and a carbon source (e.g., acetylene, ethylene, methane and other hydrocarbons).

Example 3

Preparation of Carbon Nanotube-Conducting Polymer Composite Electrodes

Electrochemical polymerization onto the carbon nanotube electrodes (applicable to all the electrodes discussed above) was carried out by the oxidation of aniline (0.1 M) in a solution containing 1 M H$_2$SO$_4$ in a pH 7.0 buffer solution. A potential window of −1.04 V to 0.96 V was employed for the electropolymerization with a scan rate of 50 mV/s for 10 cycles. Electropolymerization to form the polypyrrole was carried out by the oxidation of pyrrole (0.1 M) in a solution containing 0.1 M NaClO$_4$ in a pH 7.0 buffer solution under the same electrochemical conditions. The electrodes were washed with water and dried in air.

Example 4

Preparation of an Enzyme Electrode

A biological enzyme, glucose oxidase (e.g., 5 mg/ml) was mixed with aniline (0.1 M) in a solution containing 1 M H$_2$SO$_4$ in a pH 7.0 buffer solution. A potential window of −1.04 V to 0.96 V was employed for the immobilization of the enzyme in situ with the conducting polymer onto the carbon nanotubes with a scan rate of 50 mV/s for 10 cycles. The electrode was washed with water and dried in air. The electrode is comprised of an enzyme embedded in a polymer matrix which in turn is interdispersed with the carbon nanotubes.

Example 5

Preparation of CNT-TFTs

Preparation of CNT-TFTs: Solutions of CNTs were Prepared by Suspending CNTs in a liquid matrix. This liquid matrix may contain the solvent itself, either aqueous or organic, and/or agents to help suspension and stability, including surfactants and/or polymers. CNTs were suspended in a dilute aqueous solution containing sodium-dodecyl sulfate. Suspension was aided by the use of sonication and then centrifuged to remove non-suspended material as has been reported in Haddon et al., U.S. Pat. No. 6,641,793; Lei Zhang, et al., Chem. Mater. 2004, Vol. 16, pp. 2005-2061; Jiang Zhu et al., Nano Letters, 2003; Vol. 3, No. 8, pp. 1107-1113; Furtado, et al., Journal of the American Chemical Society, 2004, Vol. 126, No. 19, pp. 6095-6105; and PCT/US03/01159.

Gum Arabic and other polymers have also been used in place sodium-dodecyl sulfate as a suspension agent for aqueous solutions. (Nativ-Roth et al., Journal of Polymer Engineering, Vol. 22, No. 5, pp. 353-368, 2002; and Nativ-Roth et al, Nano Letters, Vol. 2, No. 1, pp. 25-28, 2002; and U.S. Patent Publication 20040131859).

Substrates were prepared and CNT films were deposited using similar methods to those published in Lay et al., Nano Lett. 2004 (4) 603 and Novak et al., Solid State Elec, 2004, in press. Surface modifications comprising the polymers and sensing elements were added to the substrates and CNT films.

Example 6

Polymerization of Conducting Polymers

Electrochemical polymerization of conducting polymers was carried out by the oxidation of the polymer monomer unit. For example, aniline (0.1 M in 1 M $H_2SO_4$) can be oxidized to polyanailine (PANI) using a cyclic voltammetry window between −1 and +1 V (vs. Ag/AgCl reference electrode). It is foreseen that other polymers could be used in the present invention. This electrochemical polymerization can be performed with other monomers, conditions and counter ions in solution. Varying the sweep rate and the number of cycles will vary the thickness of the polymer formed. The substrate can be used as the working electrode where the polymerization takes place. Chemical polymerizations can also be performed using the correct reducing agent mixed in solution with the polymer monomer. For example, KFeCN can be used to polymerize pyrrole. Additional agents can be added and co-polymerized with the conducting polymer. Additional agents include but are not limited to specific biological enzymes that can be mixed with the aniline monomer during polymerization. This creates a polymer film with an embedded enzyme. The enzyme does not loose any function or reactivity. This enzyme or the enzyme imbedded in the polymer can be used as a sensing element (E).

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method of detecting an analyte comprising the steps of:
immobilizing a polymer and sensing element to carbon nanotubes lacking alignment; and utilizing a transduction mechanism to detect the analyte, wherein the transduction mechanism uses a thin film transistor.

2. The method of claim 1 wherein the thin film transistor comprises:
a gate metal layer;
a gate dielectric layer;
a channel layer comprising the polymer, the sensing element, and the carbon nanotubes lacking alignment; and
source and drain electrodes.

3. The method of claim 1 wherein the sensing element is embedded in the polymer.

4. The method of claim 1 wherein the sensing element is an enzyme, antibody, or nucleic acid.

5. The method of claim 1 wherein the sensing element is an enzyme and the enzyme is an Oxidoreductase, Transferase, Hydrolase, Lyase, Isomerase, Ligase, Dehydrogenase, Glycosidase, Kinase, Luciferase, Lysing Enzyme, Oxidase, or Protease.

6. The method of claim 1 wherein the sensing element is an enzyme and the enzyme is glucose oxidase, glucose dehydrogenase, lactate oxidase, lactate dehydrogenase, tryosinase (polyphenol oxidase), urease, ascorbic oxidase, cholesterol oxidase, cholesterol dehydrogenase, fructose dehydrogenase, lipase, uricase, choline oxidase, pepsin, glutamate oxidase, alcohol dehydrogenase, alcohol oxidase, carbon monoxide dehydrogenase, invertase, mutarose, malate oxidase, NADH oxidase, lysine oxidase, glycerol dehydrogenase, citrate lyase, pyruvate oxidase, sulphite oxidase, amyloglucosidase, α-amylase, glucose oxidase, immobilized penicillin acylase, butyrylcholine esterase, choline oxidase, diamine oxidase, amyloglucose oxidase, laccase, formate dehydrogenase or horseradish peroxidase.

7. The method of claim 1 wherein the sensing element is DNA or RNA.

8. The method of claim 1 wherein the sensing element is an antibody and the antibody is immobilized with a polymer on the carbon nanotube.

9. An electrolytic cell comprising:
a working electrode consisting essentially of a polymer and sensing element immobilized to the carbon nanotubes lacking alignment;
a counter electrode;
a reference electrode,
and a transduction mechanism to detect oxidation of hydrogen peroxide.

10. A method of detecting hydrogen peroxide presence in a test sample comprising:
contacting a working electrode consisting essentially of carbon nanotubes lacking alignment with the test sample; and
utilizing a transduction mechanism to detect oxidation of the hydrogen peroxide.

11. A method of detecting hydrogen peroxide presence in a test sample at an anodic potential of 0.2 to 0.4 V comprising:
contacting the test sample with an electrode consisting essentially of carbon nanotube paste electrodes having about 50% by weight carbon nanotubes lacking alignment; and
utilizing a transduction mechanism to detect oxidation of the hydrogen peroxide.

* * * * *